United States Patent
Simpson et al.

(10) Patent No.: US 8,485,016 B2
(45) Date of Patent: Jul. 16, 2013

(54) METHOD OF CALIBRATING A BIOMETRIC DEVICE

(76) Inventors: Trefford Simpson, Waterloo (CA); Amir Moezzi, Waterloo (CA)

( * ) Notice: Subject to any disclaimer, the term of this patent is extended or adjusted under 35 U.S.C. 154(b) by 1205 days.

(21) Appl. No.: 12/308,053

(22) PCT Filed: Jun. 11, 2007

(86) PCT No.: PCT/CA2007/001041
§ 371 (c)(1),
(2), (4) Date: Dec. 5, 2008

(87) PCT Pub. No.: WO2007/143831
PCT Pub. Date: Dec. 21, 2007

(65) Prior Publication Data
US 2009/0163796 A1    Jun. 25, 2009

Related U.S. Application Data

(60) Provisional application No. 60/812,619, filed on Jun. 12, 2006.

(51) Int. Cl.
*G01B 11/00* (2006.01)
(52) U.S. Cl.
USPC .......................................................... 73/1.79
(58) Field of Classification Search
None
See application file for complete search history.

(56) References Cited

U.S. PATENT DOCUMENTS

| 6,530,266 | B1 * | 3/2003 | Adderton et al. | 73/105 |
| 6,816,605 | B2 | 11/2004 | Rowe et al. | |
| 6,823,305 | B2 * | 11/2004 | Eide | 704/234 |
| 7,029,444 | B2 | 4/2006 | Shin et al. | |
| 7,401,496 | B2 * | 7/2008 | Ho et al. | 73/1.79 |
| 7,810,382 | B2 * | 10/2010 | Schimmel et al. | 73/105 |
| 7,929,661 | B2 * | 4/2011 | Borghese et al. | 378/38 |
| 2004/0133944 | A1 * | 7/2004 | Hake et al. | 800/281 |

FOREIGN PATENT DOCUMENTS

| EP | 1452135 | 9/2004 |
| WO | WO 2007/143831 | 12/2007 |

OTHER PUBLICATIONS

Bechmann M, et al. "Central corneal thickness measurement with a retinal optical coherence tomography device versus standard ultrasonic pachymetry". Cornea 2001;20:50-4.
Doughty MJ, Zaman ML. "Human corneal thickness and its impact on intraocular pressure measures: a review and meta-analysis approach." Surv Ophthalmol 2000;44:367-408.
Marsich MW, Bullimore MA. "The repeatability of corneal thickness measures." Cornea 2000;17:792-5.

(Continued)

*Primary Examiner* — Robert R Raevis

(57) ABSTRACT

A method of calibrating a biometric device useful to measure a target dimension of a physiological tissue is provided comprising the steps of: measuring the target dimension of at least two samples of a reference material with the device to provide an actual output, wherein the reference material possesses at least one property of the tissue required for the function of the device and wherein each of the samples has a known target dimension; calculating a calibration equation based on the actual output of the device and the known target dimensions of the samples; and adjusting the actual output of the device according to the calibration equation to yield a corrected output. The calibration method provides a means of obtaining accurate tissue measurements. Also provided is a method of using a biometric device to measure a target dimension of a physiological tissue which incorporates calibration.

11 Claims, 2 Drawing Sheets

OTHER PUBLICATIONS

Wang J, et al. "Relation between optical coherence tomography and optical pachymetry measurements of corneal swelling induced by hypoxia". Am J Ophthalmol 2002;134:93-8.

Wong AC, et al. "Correlational study of central corneal thickness measurements on Hong Kong Chinese using optical coherence tomography, Orbscan and ultrasound pachymetry." Eye 2002;16:715-21.

Muscat S, et al. "Repeatability and reproducibility of corneal thickness measurements by optical coherence tomography." Invest Ophthalmol Vis Sci 2002;43:1791-5.

Drexler W, et al. "Ultrahigh-resolution ophthalmic optical coherence tomography". Nat Med 2001;7:502-7.

Lattimore MR Jr, et al. "Orbscan pachymetry: implications of a repeated measures and diurnal variation analysis." Ophthalmology 1999;106:977-81.

Li HF, et al. "Epithelial and corneal thickness measurements by in vivo confocal microscopy through focusing (CMTF)". Curr Eye Res 1997;16:214-21.

Maldonado MJ, et al. "Optical coherence tomography evaluation of the corneal cap and stromal bed features after laser in situ keratomileusis for high myopia and astigmatism." Ophthalmology 2000;107:81-7.

Moezzi AM. "Contact lens induced corneal swelling measured with Orbscan II corneal topographer [Master's thesis]." University of Waterloo, Canada; 2002.

Olsen T, Nielsen CB, Ehlers N. "On the optical measurement of a corneal thickness. I. Optical principle and sources of error." Acta Ophthalmol (Copenh) 1980;58:760-6.

Reinstein DZ, et al. "Epithelial and corneal thickness measurements by high-frequency ultrasound digital signal processing." Ophthalmology 1994;101:140-6.

Reinstein DZ, Silverman RH, Trokel SL, Coleman DJ. "Corneal pachymetric topography." Ophthalmology 1994;101:432-8.

Simpson T, Sin S. "Repeatability of corneal and epithelial thickness using OCT." Optom Vis Sci 2002;79(suppl):7.

Stark WJ, Gilbert ML, Gottsch JD, Munnerlyn C. "Optical pachometry in the measurement of anterior corneal disease: an evaluative tool for phototherapeutic keratectomy." Arch Ophthalmol 1990;108:12-3.

Wang J, Fonn D, Simpson TL, Jones L. "The measurement of corneal epithelial thickness in response to hypoxia using optical coherence tomography." Am J Ophthalmol 2002;133:315-9.

Wang J, Fonn D, Simpson TL. "Topographical thickness of the epithelium and total cornea after hydrogel and PMMA contact lens wear with eye closure." Invest Ophthalmol Vis Sci 2003;44:1070-4.

Wilson G, O'Leary DJ, Henson D. "Micropachometry: a technique for measuring the thickness of the corneal epithelium." Invest Ophthalmol Vis Sci 1980;19:414-7.

Swarbrick HA, Wong G, O'Leary DJ. "Corneal response to orthokeratology." Optom Vis Sci 1998;75:791-9.

Gordon A, Boggess A, Molinari JF. "Variability of ultrasonic pachometry." Optom Vis Sci 1990;67:162-5.

Hulley S, Martin JN, Cummings S. "Planning the measurements: precision and accuracy." In: Hulley S, ed. Designing Clinical Research: An Epidemiologic Approach, 2nd ed. Philadelphia: Lippincott Williams & Wilkins; 2001:37-50.

Edmund C, la Cour M. "Some components affecting the precision of corneal thickness measurement performed by optical pachometry." Acta Ophthalmol (Copenh) 1986;64:499-503.

Olsen T, Nielsen CB, Ehlers N. "On the optical measurement of corneal thickness." II. The measuring conditions and sources of error. Acta Ophthalmol (Copenh) 1980;58:975-84.

* cited by examiner

METHOD OF CALIBRATING A BIOMETRIC DEVICE

FIELD OF THE INVENTION

The present invention relates to a novel method of calibrating a biometric device, as well as a method of accurately measuring a target dimension of a physiological tissue which incorporates calibration.

BACKGROUND OF THE INVENTION

Measurement of a dimension of a physiological tissue, such as a mammalian tissue, can have important clinical and research applications in a variety of diagnostic and therapeutic fields. For example, measurement of corneal thickness may have applications in the diagnosis and/or treatment of conditions in the field of optometry or ophthalmology such as glaucoma, corneal pathology, refractive surgery and contact lenses. However, despite strong associations among measurements of central corneal thickness by different techniques,[1-6] there is a lack of a gold standard for cross-calibration between different instruments.

Although there is abundant literature on precision (repeatability or reliability) of the common biometric equipment for measuring different tissues including corneal thickness[3,6-21], no information about accuracy of the methods exists. Precision quantifies how multiple measures compare with each other. Accuracy is an indicator of the proximity of the measurement to the real physical value that is being measured. A measurement method could be precise but not accurate.[22,23] For example, a piece of equipment could always underestimate corneal thickness by, say, 40 μm and be very precise (repeatable) for this measurement, which is not accurate. However, the question is whether a refractive surgeon or a glaucoma specialist can make a sound clinical decision based on this measurement, particularly in borderline cases. Therefore, in addition to the importance of precision, a measurement technique should also be accurate and its calibration should be verifiable using a gold standard.

Currently, a non-invasive method for comparing tissue measurements taken by different biometric devices does not exist. Such a comparison can only be conducted by obtaining a sample of the subject tissue, for example, by biopsy. This method of comparison is neither acceptable nor feasible in the case of certain tissue types such as the ocular tissue.

It would, thus, be desirable to develop a method of using a biometric device which renders accurate results that can be validly compared with similar results obtained using different devices.

SUMMARY OF THE INVENTION

Accordingly, a novel method of calibrating a biometric device useful to measure dimensions of physiological tissue has now been developed. The calibration utilizes samples of a reference material that possess a property of the physiological tissue that is required for the function of the device.

Thus, in one aspect, a method of calibrating a biometric device useful to measure a target dimension of a physiological tissue is provided comprising:
 (i) measuring the target dimension of at least two samples of a reference material with the device to provide an actual output, wherein the reference material possesses at least one property of the tissue required for the function of the device and wherein each of the samples has a known target dimension;
 (ii) calculating a calibration equation based on the actual output of the device and the known target dimensions of the samples; and
 (iii) adjusting the actual output of the device according to the calibration equation to yield a corrected output.

In another aspect of the present invention, a method of measuring a target dimension of a physiological tissue using a biometric device is provided. The method comprises the steps of:
 (i) measuring the target dimension of at least two samples of a reference material with the device to provide an actual output, wherein the reference material possesses at least one property of the tissue required for the function of the device and wherein each of the samples has a known target dimension;
 (ii) calculating a calibration equation based on the actual output of the device and the known target dimensions of the samples;
 (iii) adjusting the actual output of the device according to the calibration equation to yield a corrected output; and
 (iv) measuring the target dimension of the tissue with the device, wherein the measured dimension is corrected according to the calibration equation.

In another aspect of the invention, a method of cross-calibrating multiple biometric devices which measure the same dimension of a target tissue, but which function differently, is provided. The method comprises calibrating the biometric devices as described utilizing a reference material having properties of the target tissue required for the function of each of the biometric devices.

The present invention advantageously provides a means of calibrating a biometric device that can be incorporated into a method of measuring a target dimension of a physiological tissue to yield accurate measured values of a selected tissue dimension. The present invention allows rapid and simple calibration of measurements obtained with biometric devices that utilize both the same and different working principles so that measurements from different devices may be used interchangeably when measuring the same target tissue. In addition, device accuracy may be verified using the methods disclosed herein.

These and other aspects of the present invention will be described by reference to the following drawings in which:

DETAILED DESCRIPTION OF THE INVENTION

Figure 1:
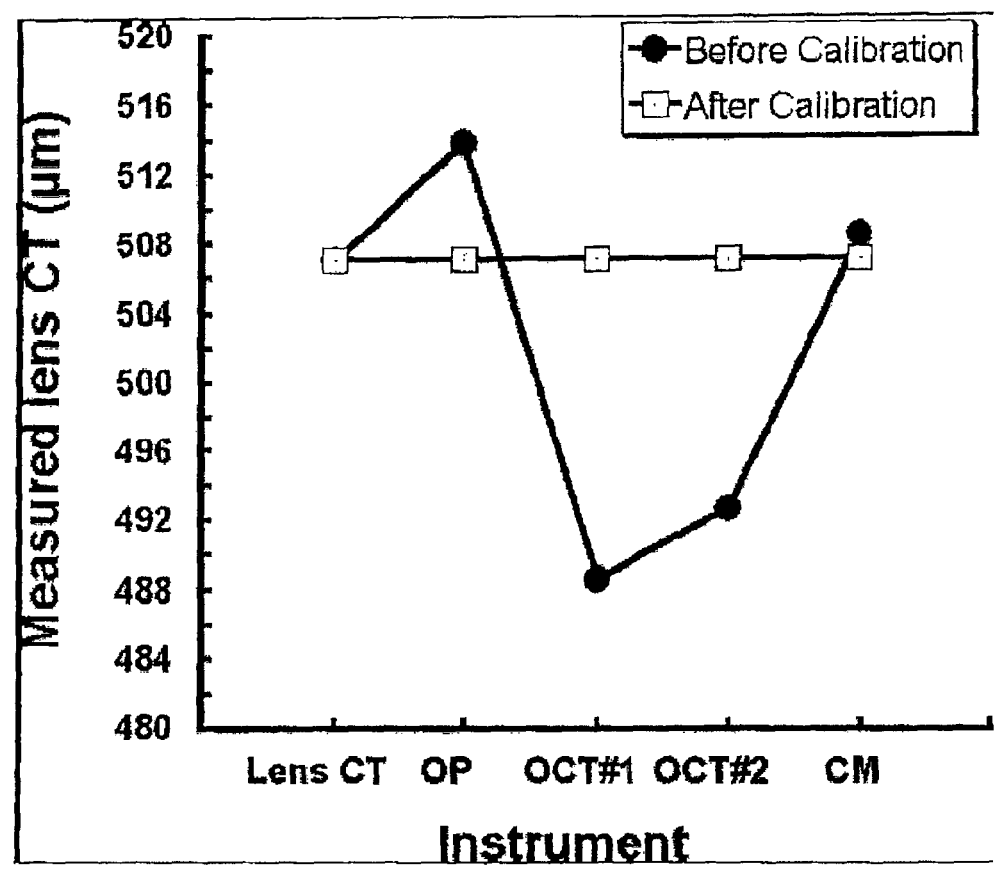
FIG. 1 graphically compares measured corneal thickness with different instruments before and after instrument calibration according to the present invention.

A method of calibrating a biometric device useful to measure a target dimension of a physiological tissue is provided. The method makes use of a reference material having a known target dimension (a real target dimension) that possesses at least one property of the tissue required for the function of the device. The calibration method comprises measuring the target dimension of at least two samples of the reference material with the device to generate an actual output. A calibration equation is then calculated based on the actual output of the device and the known or real target dimensions of the samples; and adjusting the actual output of the device according to the calibration equation to yield a corrected or real output.

The term "biometric device" is used herein generally to encompass devices used to measure a dimension of a physiological tissue. An optical biometric device, for example, can measure a dimension, such as thickness, of parts of the eye including, but not limited to, the retina, iris, crystalline lens and cornea. Examples of optical biometric devices include, but are not limited to, pachometers, interferometric devices such as optical coherence tomographers (OCT's), scanning slit imaging devices, confocal microscopes and Scheimpflug devices. Other biometric devices include, but are not limited to, acoustic biometric devices, ultra-sound biometric devices, x-ray imaging devices, which measure the permeability of tissue, magnetic resonance imagers, which can be used to measure a number of dimensions of physiological tissue, and other non-visual electromagnetic devices.

The term "dimension" refers to a physical characteristic of a physiological tissue that can be measured. One of skill in the art will be familiar with the various dimensions of tissue that can be measured. Examples include, but are not limited to thickness, length, curvature, shape and permeability.
The physiological tissue may be any tissue subject to measurement by a biometric device. Examples include, but are not limited to, epidermal tissue, connective tissue, muscle tissue, vascular tissue, nervous tissue, and specific tissue types such as ocular tissue, including corneal, retinal and lens tissue, and aqueous and/or vitreous humour.

The present method relates to the calibration of a biometric device for use in measuring a target dimension of a physiological tissue. To calibrate the device, the device is used to measure the target dimension of a reference material in which the target dimension is already known, i.e. measured by other means known to be accurate. The calibration will generally involve measurement using the biometric device of at least 2, and preferably 3 to 4, samples of a selected reference material with a target dimension that is known but which is different in each case. The known or real target dimensions generally span the range of expected measurements of the target dimension.

In order to be effective, the reference material will possess at least one property of the target physiological tissue that is required for the function of the biometric device. For example, for an optical biometric device, the reference material will possess a refractive index equal to the refractive index (RI) of the target tissue. The overall RI of corneal tissue is generally accepted to be 1.376. Thus, a reference material for the measurement of corneal tissue may have an RI of, for example, 1.376. For the calibration of optical devices, the reference material is preferably a transparent, semi-transparent or opaque material that is readily measurable by the biometric device, for example, plastic, glass, fluid, or gas. The reference material may be layered to mimic the composition of the target tissue, for example, corneal tissue which comprises multiple layers. For an acoustic biometric device, such as an ultrasound pachometer, the reference material will possess an acoustic density equal to that of the target tissue. For an x-ray imaging device, the reference material will possess the x-ray characteristics of the target tissue.

The method is also useful to cross-calibrate biometric devices that measure the same dimension of a target tissue, but which function differently, e.g. an optical biometric device and a non-optical biometric device including, but not limited to, an acoustic, ultrasonic, magnetic, or non-visual electromagnetic biometric device. To conduct such a cross-calibration, the reference material must have properties of the target tissue required for the function of both devices. To cross-calibrate an optical biometric device and a non-optical biometric device, thus, the reference material must have both the refractive index and additionally the non-optical characteristic required for use of the selected non-optical biometric device. For example, to cross-calibrate an optical biometric device and an acoustic biometric device for measuring ocular tissue, thus, the reference material must have both the refractive index and acoustic density of the target ocular tissue.

The data obtained from measuring the target dimension of the reference material samples, i.e. the actual output, and the known target dimensions of the samples are both used to prepare a calibration equation. The calibration equation defines the relationship between the actual output of the biometric device and the actual or known target dimensions, and is used to modify the actual output to a corrected output that corresponds with the known or actual target dimension within an acceptable amount of error or an amount of error that may not be considered statistically significant. The accuracy of this calibration method will depend on the number of samples of the reference material which are being measured. As one of skill in the art will appreciate, the calibration equation will vary with the biometric device being calibrated and the target physiological tissue being measured.

Following measurement of the reference material samples, the biometric device can be used to measure the same dimension, i.e. the target dimension, in the selected physiological tissue. The measurements of the target dimension of the tissue are then adjusted in accordance with the calibration equation in order to yield an accurate measurement of the target dimension, i.e. a corrected output. Following calibration according to the present method, the corrected output will have a value that corresponds with the known or real target dimension within an acceptable range of error, e.g. which may be statistically insignificant.

The present invention can be broadly utilized at the manufacturing level of a biometric device as well as at the user level. The method advantageously provides a non-invasive method of calibrating a biometric device as well as a means of cross-calibrating between biometric devices that measure the same characteristic such that regardless of the device being used, the absolute values of biometric measurements are not significantly different between devices. This will aid manufacturers in accurately cross-calibrating different biometric devices. Clinicians and researchers will also have a means to verify a calibration as well as recalibrating a device as needed.

Improved accuracy of biometric measurements using the present technique provides enhanced validity of data for clinical decision making and improves the quality of care for patients. In addition, this method will allow consistent calibration of biometric devices for comparison with historical data. The same level of accuracy and consistency can be applied to a research setting using the present method to allow accurate comparison and universal interpretation of data from different clinics/studies using different biometric devices if they are similarly calibrated using the present methodology.

As one of skill in the art will appreciate, the above disclosure generally describes aspects of the invention. It is believed that one of ordinary skill in the art may, using the preceding description, make and use these aspects of the invention. In addition, certain embodiments of the invention have been described; however, other embodiments may exist which also fall within the scope of the appended claims. For example, changes in form and substitution of equivalents which do not depart from the scope of the claims are also contemplated. All journal articles and other documents such as patents or patent applications referred to herein are hereby incorporated by reference.

Embodiments of the present invention are described by reference to the following specific example which is not to be construed as limiting.

Example 1

Methods

Instrumentation and Lenses

Fourteen rigid lenses of different thicknesses were manufactured using a plastic material with refractive index (RI) of 1.3760+/−0.0005 (at 589 nm). This plastic material was developed by Optical Polymer Research, Inc., Gainesville, Fla. All lenses were made in piano power with a base curve of 8.6 mm and no prism. Physical center thickness of the calibration lenses (ranging from 301 to 696 μm) was measured using a precision mechanical gauge (Vigor GA-715; Japan) and the physical thickness of each lens was derived from the average of three measurements (Table 1).

TABLE 1

Lens center thickness (μm)

| Lens No. | Center Thickness (μm) |
|---|---|
| 1 | 301 |
| 2 | 336 |
| 3 | 362 |
| 4 | 415 |
| 5 | 470 |
| 6 | 478 |
| 7 | 489 |
| 8 | 527 |
| 9 | 551 |
| 10 | 580 |
| 11 | 608 |
| 12 | 635 |
| 13 | 650 |
| 14 | 696 |
| Mean | 507 |
| Standard deviation | 122 |

Center thickness (CT) of the same set of lenses was measured using a computerized optical pachometer (OP) mounted onto a Zeiss 30 SL-M biomicroscope, two different Zeiss-Humphrey OCTII optical coherence tomographers (OCTs), and a Nidek Confoscan3 confocal microscope (CM).

Procedure

The lenses were installed onto a wheel in a random order. A number was assigned to each lens with no reference to the thickness of the lens. All the measurements on OP were completed by one operator and all the measurements on OCT 1, OCT 2 and CM was performed by a second operator. All lenses were measured once at each station. The number of measurements per lens was selected based on the research protocols as used for each device in the Centre for Contact Lens Research (CCLR). Therefore, more measurements were required for the OP because of high measurement variability, which was reported for OP in the literature.[23,24]

Seven consecutive measurements for each lens were taken by the OP and the lens CT was derived from the average of five readings after the computer trimmed the highest and the lowest readings.

For each lens, only one measurement was taken by each OCT machine. One hundred axial scans (1.13-mm width) were processed and lens CT was obtained using custom software.

For the CM, lens CT was measured after applying a drop of a gonioscopy gel to the posterior surface of the lens and stepping through the lens manually from anterior to posterior surfaces. One measurement was taken for each lens.

Accuracy of measurements of the four instruments was determined by comparison to the physical CT of the lenses.

Center thickness of the same set of lenses was measured again after each instrument was calibrated. Accuracy of measurements was compared among the four instruments.

Data Analysis

Using a repeated-measures analysis of variance, the effects of measurement device were examined. p values <0.05 were considered statistically significant. Post hoc paired t-tests with Bonferroni correction (significance level p<0.01) were used to determine the significance of specific pairs.

Results

The values quoted in this section are the mean+/−standard deviation of lens CT, unless otherwise stated.

Before calibrating the machines, there was a significant effect of the measurement device (p<0.05). There was a significant difference in lens center thickness between OP and each OCT as well as between the two OCT machines (all post hoc tests; p<0.01). CM was not significantly different from OP (post hoc test; p>0.01) but was significantly different from each OCT (post hoc tests; p<0.01), (see FIG. 1 and Table 2 below).

TABLE 2

Lens center thickness (μm) by each instrument (mean +/− standard deviation) before calibration

| | Lens Center Thickness | Optical Pacho-meter | Optical Coherence Tomo-grapher 1 | Optical Coherence Tomo-grapher 2 | Confocal |
|---|---|---|---|---|---|
| Mean | 507.1 | 513.8 | 488.6 | 492.6 | 508.5 |
| Standard deviation | 122.1 | 118.0 | 116.4 | 118.1 | 120.6 |

The differences between instruments were eliminated (p>0.05) after applying calibration equations (Table 3 below) for each device (FIG. 1), which were derived through linear regression analysis of lens physical center thickness (known) and instrument measured center thickness (actual output of the device).

TABLE 3

Calibration equations[a]

| Device | Calibration Equation |
|---|---|
| Optical pachometer | Calibrated CT = −24.2965 + 1.0342 × measured CT |
| Optical coherence tomographer 1 | Calibrated CT = −5.2248 + 1.0486 × measured CT |
| Optical coherence tomographer 2 | Calibrated CT = −2.1211 + 1.0338 × measured CT |
| Confocal microscope | Calibrated CT = 1.4079 + 0.9945 × measured CT |

[a]Note that these are not general equations for the devices. These equations are specific for individual instruments.
CT, center thickness In addition, after each instrument was calibrated with lenses of 1.376 refractive index, there was no significant difference (p>0.05) between mean measured values of lens center thickness by OP, each OCT, CM, and the physical center thickness of the lenses (Table 4 below).

TABLE 4

Lens center thickness (μm) by each instrument
(mean +/− standard deviation) after calibration

|  | Lens Center Thickness | Optical Pachometer | Optical Coherence Tomographer 1 | Optical Coherence Tomographer 2 | Confocal |
|---|---|---|---|---|---|
| Mean | 507.1 | 507.1 | 507.1 | 507.1 | 507.1 |
| Standard deviation | 122.1 | 122.1 | 122.1 | 122.1 | 119.9 |

Figure 2:
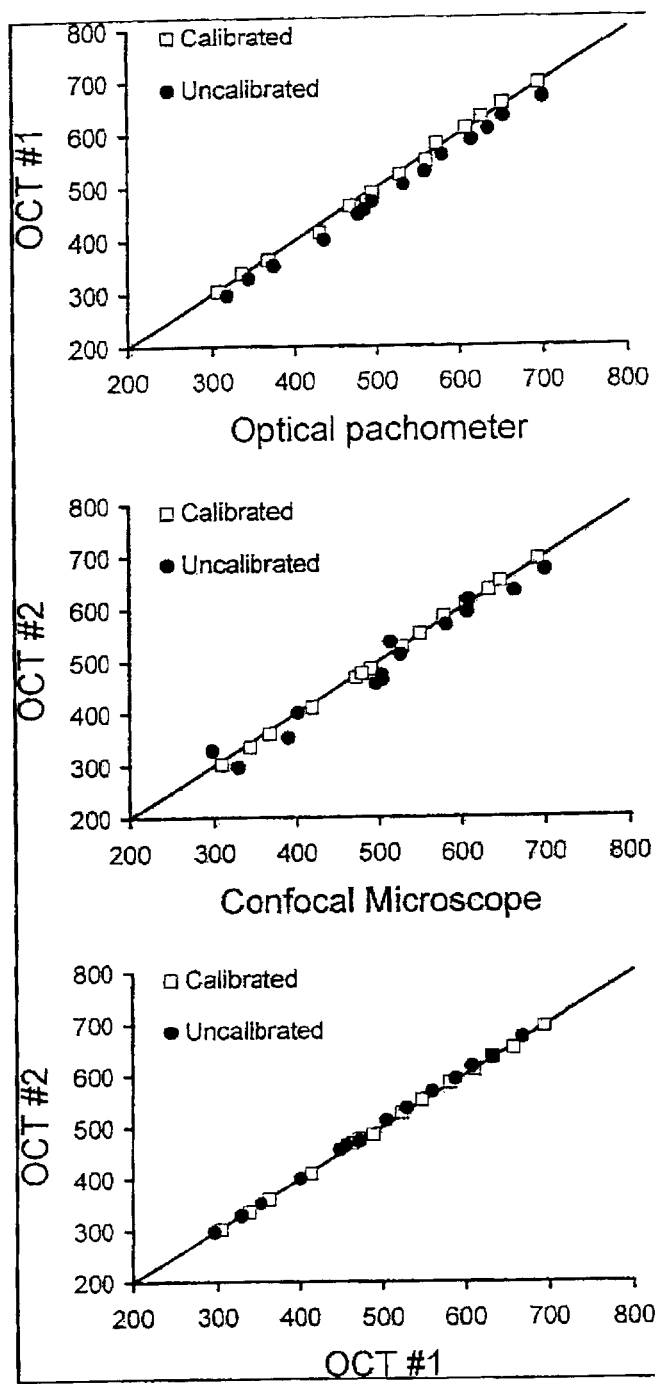
FIG. 2 provides a graphic comparison of the correlation between calibrated and uncalibrated instruments for lens center thickness measurements.

There were significant correlations ($p<0.05$) between each pair of the instruments for measured CT values both before and after calibration (see FIG. 2).

Improved accuracy using the present method is clearly shown by comparing real thickness of the reference material to the measured values by each device before and after calibration (Table 2 vs. Table 4 as well as FIG. 1). In addition, the mean (±standard deviation) percentage difference between measured values by each device and the physical thickness of the lenses can be shown by the two following tables (Table 5 and 6) which are based on the following formula:

Percent difference=100 measured value by the device-physical thickness of the lens/physical thickness of the lens

TABLE 5

Deviation (%) from physical lens center thickness by each instrument
(mean ± standard deviation) before calibration

|  | Optical Pachometer | Optical Coherence Tomographer 1 | Optical Coherence Tomographer 2 | Confocal |
|---|---|---|---|---|
| Mean Δ | 1.63% | −3.56% | −2.83% | 0.48% |
| Standard deviation | 1.67% | 0.88% | 0.53% | 5.64% |

TABLE 6

Deviation (%) from physical lens center thickness by each instrument
(mean ± standard deviation) after calibration

|  | Optical Pachometer | Optical Coherence Tomographer 1 | Optical Coherence Tomographer 2 | Confocal |
|---|---|---|---|---|
| Mean Δ | 0.01% | 0.03% | 0.01% | 0.22% |
| Standard deviation | 0.97% | 0.78% | 0.52% | 5.62% |

The results of the present study demonstrate that using calibration lenses with the same refractive index as the cornea (1.376) allows rapid and simple calibration of the pachometers using different optical principles so that corneal thickness measurements from different optical devices may be used interchangeably.

Example 2

This is an example of applying the calibration equations to human central corneal thickness measurements (CCT) by the two OCT machines from Example 1. The values in the following table are the central corneal thickness in microns. The following equations (from Example 1, Table 3) were used which were derived from calibrating each machine with the RI 1.376 lenses.

For OCT 1:

Real lens CT=−5.2248+1.0486×measured value of lens CT by the machine.

Therefore:

Human CCT after calibration=−5.2248+1.0486×measured human CCT before calibration.

For OCT2:

Real lens CT=−2.1211+1.0338×measured value of lens CT by the machine.

Therefore:

Human CCT after calibration=−2.1211+1.0338×measured human CCT before calibration.

TABLE 7

|  | Uncalibrated CT | | Calibrated CT | |
|---|---|---|---|---|
| ID # | OCT #1 | OCT #2 | OCT #1 | OCT #2 |
| 1 | 500 | 512 | 519.1 | 527.2 |
| 2 | 512 | 520 | 531.7 | 535.5 |
| 3 | 496 | 500 | 514.9 | 514.8 |
| 4 | 492 | 500 | 510.7 | 514.8 |
| 5 | 472 | 520 | 489.7 | 535.5 |
| 6 | 464 | 536 | 481.3 | 552.0 |
| 7 | 520 | 480 | 540.0 | 494.1 |
| 8 | 528 | 472 | 548.4 | 485.8 |
| 9 | 552 | 540 | 573.6 | 556.1 |
| 10 | 536 | 540 | 556.8 | 556.1 |
| 11 | 520 | 516 | 540.0 | 531.3 |
| 12 | 504 | 520 | 523.3 | 535.5 |
| 13 | 520 | 528 | 540.0 | 543.7 |
| 14 | 520 | 528 | 540.0 | 543.7 |
| 15 | 480 | 484 | 498.1 | 498.2 |
| 16 | 488 | 488 | 506.5 | 502.4 |
| 17 | 496 | 504 | 514.9 | 518.9 |
| 18 | 504 | 512 | 523.3 | 527.2 |
| 19 | 480 | 488 | 498.1 | 502.4 |
| 20 | 496 | 512 | 514.9 | 527.2 |
| 21 | 488 | 492 | 506.5 | 506.5 |
| 22 | 488 | 496 | 506.5 | 510.6 |
| 23 | 512 | 504 | 531.7 | 518.9 |
| 24 | 512 | 512 | 531.7 | 527.2 |
| 25 | 512 | 520 | 531.7 | 535.5 |
| 26 | 520 | 520 | 540.0 | 535.5 |
| 27 | 480 | 488 | 498.1 | 502.4 |
| 28 | 484 | 488 | 502.3 | 502.4 |
| 29 | 496 | 504 | 514.9 | 518.9 |
| 30 | 496 | 504 | 514.9 | 518.9 |
| 31 | 520 | 520 | 540.0 | 535.5 |
| 32 | 528 | 524 | 548.4 | 539.6 |
| 33 | 552 | 552 | 573.6 | 568.5 |
| 34 | 552 | 556 | 573.6 | 572.7 |
| 35 | 504 | 504 | 523.3 | 518.9 |
| 36 | 504 | 500 | 523.3 | 514.8 |
| 37 | 532 | 528 | 552.6 | 543.7 |
| 38 | 536 | 540 | 556.8 | 556.1 |
| 39 | 456 | 456 | 472.9 | 469.3 |

TABLE 7-continued

| ID # | Uncalibrated CT | | Calibrated CT | |
|---|---|---|---|---|
| | OCT #1 | OCT #2 | OCT #1 | OCT #2 |
| 40 | 456 | 464 | 472.9 | 477.6 |
| 41 | 504 | 496 | 523.3 | 510.6 |
| 42 | 496 | 496 | 514.9 | 510.6 |
| 43 | 504 | 504 | 523.3 | 518.9 |
| 44 | 496 | 500 | 514.9 | 514.8 |
| 45 | 520 | 528 | 540.0 | 543.7 |
| 46 | 520 | 520 | 540.0 | 535.5 |
| 47 | 488 | 496 | 506.5 | 510.6 |
| 48 | 488 | 492 | 506.5 | 506.5 |
| 49 | 488 | 512 | 506.5 | 527.2 |
| 50 | 504 | 508 | 523.3 | 523.0 |
| 51 | 528 | 536 | 548.4 | 552.0 |
| 52 | 528 | 536 | 548.4 | 552.0 |
| 53 | 480 | 488 | 498.1 | 502.4 |
| 54 | 488 | 488 | 506.5 | 502.4 |
| 55 | 592 | 596 | 615.5 | 614.0 |
| 56 | 548 | 552 | 569.4 | 568.5 |
| 57 | 532 | 544 | 552.6 | 560.3 |
| 58 | 528 | 536 | 548.4 | 552.0 |
| 59 | 504 | 504 | 523.3 | 518.9 |
| 60 | 504 | 504 | 523.3 | 518.9 |
| 61 | 528 | 528 | 548.4 | 543.7 |
| 62 | 520 | 532 | 540.0 | 547.9 |
| 63 | 496 | 496 | 514.9 | 510.6 |
| 64 | 488 | 500 | 506.5 | 514.8 |
| Mean | 507.5 | 511.9 | 526.9 | 527.1 |
| SD | 24.6 | 23.8 | 25.8 | 24.6 |
| Paired t-test | $p = 0.022$ | | $p = 0.928$ | |

The "uncalibrated" columns in the above table show human (in vivo) corneal thickness measurements in two devices "calibrated" by the manufacturer. Despite this, there are clear (statistical) differences between measurements (uncalibrated OCT#1 and OCT#2 columns in the above table).

After applying the present calibration technique, there are no differences (statistically) between these devices when measuring the corneal thickness (calibrated OCT#1 and OCT#2 columns in the above table).

REFERENCES

1. Bechmann M, Thiel M J, Neubauer A S, Ullrich S, Ludwig K, Kenyon K R, Ulbig M W. Central corneal thickness measurement with a retinal optical coherence tomography device versus standard ultrasonic pachymetry. Cornea 2001; 20:50-4.
2. Doughty M J, Zaman M L. Human corneal thickness and its impact on intraocular pressure measures: a review and meta-analysis approach. Surv Opthalmol 2000; 44:367-408.
3. Marsich M W, Bullimore M A. The repeatability of corneal thickness measures. Cornea 2000; 17:792-5.
4. Wang J, Form D, Simpson T L, Jones L. Relation between optical coherence tomography and optical pachymetry measurements of corneal swelling induced by hypoxia. Am J Opthalmol 2002; 134:93-8.
5. Wong A C, Wong C C, Yuen N S, Hui S P. Correlational study of central corneal thickness measurements on Hong Kong Chinese using optical coherence tomography, Orbscan and ultrasound pachymetry. Eye 2002; 16:715-21.
6. Muscat S, McKay N, Parks S, Kemp E, Keating D. Repeatability and reproducibility of corneal thickness measurements by optical coherence tomography. Invest Opthalmol Vis Sci 2002; 43:1791-5.
7. Drexler W, Morgner U, Ghanta R K, Kartner F X, Schuman J S, Fujimoto J G. Ultrahigh-resolution ophthalmic optical coherence tomography. Nat Med 2001; 7:502-7.
8. Lattimore M R Jr, Kaupp S, Schallhorn S, Lewis R T. Orbscan pachymetry: implications of a repeated measures and diurnal variation analysis. Opthalmology 1999: 106:977-81.
9. Li H F, Petroll W M, Moller-Pedersen T, Maurer J K, Cavanagh H D, Jester J V. Epithelial and corneal thickness measurements by in vivo confocal microscopy through focusing (CMTF). Curr Eye Res 1997; 16:214-21.
10. Maldonado M J, Ruiz-Oblitas L, Munuera J M, Aliseda D, Garcia-Layana A, Moreno-Montanes J. Optical coherence tomography evaluation of the corneal cap and stromal bed features after laser in situ keratomileusis for high myopia and astigmatism. Opthalmology 2000; 107:81-7.
11. Moezzi A M. Contact lens induced corneal swelling measured with Orbscan II corneal topographer [Master's thesis]. University of Waterloo, Canada; 2002.
12. Olsen T, Nielsen C B, Ehlers N. On the optical measurement of a corneal thickness. I. Optical principle and sources of error. Acta Opthalmol (Copenh) 1980; 58:760-6.
13. Reinstein D Z, Silverman R H, Rondeau M J, Coleman D J. Epithelial and corneal thickness measurements by high-frequency ultrasound digital signal processing. Opthalmology 1994; 101:140-6.
14. Reinstein D Z, Silverman R H, Trokel S L, Coleman D J. Corneal pachymetric topography. Opthalmology 1994; 101:432-8.
15. Simpson T, Sin S. Repeatability of corneal and epithelial thickness using OCT. Optom Vis Sci 2002; 79(suppl):7.
16. Stark W J, Gilbert M L, Gottsch J D, Munnerlyn C. Optical pachometry in the measurement of anterior corneal disease: an evaluative tool for phototherapeutic keratectomy. Arch Opthalmol 1990; 108:12-3.
17. Wang J, Form D, Simpson T L, Jones L. The measurement of corneal epithelial thickness in response to hypoxia using optical coherence tomography. Am J Opthalmol 2002; 133:315-9.
18. Wang J, Form D, Simpson T L. Topographical thickness of the epithelium and total cornea after hydrogel and PMMA contact lens wear with eye closure. Invest Opthalmol Vis Sci 2003; 44:1070-4.
19. Wilson G, O'Leary D J, Henson D. Micropachometry: a technique for measuring the thickness of the corneal epithelium. Invest Opthalmol Vis Sci 1980; 19:414-7.
20. Swarbrick H A, Wong G, O'Leary D J. Corneal response to orthokeratology. Optom Vis Sci 1998; 75:791-9.
21. Gordon A, Boggess A, Molinari J F. Variability of ultrasonic pachymetry. Optom Vis Sci 1990; 67:162-5.
22. Hulley S, Martin J N, Cummings S. Planning the measurements: precision and accuracy. In: Hulley S, ed. Designing Clinical Research: An Epidemiologic Approach, $2^{nd}$ ed. Philadelphia: Lippincott Williams & Wilkins; 2001: 37-50.
23. Edmund C, la Cour M. Some components affecting the precision of corneal thickness measurement performed by optical pachometry. Acta Opthalmol (Copenh) 1986; 64:499-503.
24. Olsen T, Nielsen C B, Ehlers N. On the optical measurement of corneal thickness. II. The measuring conditions and sources of error. Acta Opthalmol (Copenh) 1980; 58:975-84.

We claim:

1. A method of calibrating an optical biometric device useful to measure a physical characteristic of a physiological tissue comprising:
    (i) measuring the physical characteristic of at least two samples of a reference material selected from the group consisting of: plastic, glass, fluid and gas with the optical biometric device to provide an actual output, wherein the reference material possesses at least one property of the physiological tissue which is required for the function of the optical biometric device and wherein the physical characteristic of each of the samples is pre-measured,
(ii) calculating a calibration equation based on the actual output of the optical biometric device and the pre-measured physical characteristic of the samples; and
(iii) adjusting the actual output of the optical biometric device according to the calibration equation to yield a corrected output.

2. A method as defined in claim 1, wherein the optical biometric device is selected from the group consisting of: pachometers, optical coherence tomographers (OCT's), scanning slit imaging devices, confocal microscopes and Scheimpflug devices.

3. A method as defined in claim 1, wherein the reference material possesses a refractive index equal to the refractive index (RI) of the target tissue.

4. A method as defined in claim 1, wherein the physiological tissue is selected from the group consisting of epidermal tissue, connective tissue, muscle tissue, vascular tissue, nervous tissue and ocular tissue.

5. A method as defined in claim 4, wherein the ocular tissue is selected from the group consisting of corneal tissue, retinal tissue, lens tissue, aqueous humour and vitreous humour.

6. A method as defined in claim 1, wherein the physical characteristic is selected from the group consisting of: thickness, length, curvature, and shape.

7. A method as defined in claim 1, wherein the calibration equation is determined using linear regression analysis of the known physical characteristic and the actual output of the device.

8. A method as defined in claim 1, including the additional step of cross-calibrating the optical biometric device with a second biometric device which functions differently than the optical biometric device, wherein the reference material possesses properties of the target tissue required for the function of each of the optical biometric devices and the second biometric device.

9. A method as defined in claim 8, wherein the second biometric device is a non-optical device, and wherein the reference material has a refractive index and an additional non-optical characteristic of the target material that is required for the function of the second biometric device.

10. A method of measuring a physical characteristic of a physiological tissue using an optical biometric device comprising the steps of:
(i) measuring the physical characteristic of at least two samples of a reference material selected from the group consisting of: plastic, glass, fluid and gas with the optical biometric device to provide an actual output, wherein the reference material possesses at least one property of the tissue which is required for the function of the optical biometric device and wherein the physical characteristic of each of the samples is pre-measured;
(ii) calculating a calibration equation based on the actual output of the optical biometric device and the pre-measured physical characteristic of the samples;
(iii) adjusting the actual output of the optical biometric device according to the calibration equation to yield a corrected output; and
(iv) measuring the physical characteristic of the tissue with the optical biometric device, wherein the measured physical characteristic is corrected according to the calibration equation.

11. A method as defined in claim 10, wherein the reference material possesses a refractive index equal to the refractive index (RI) of the target tissue.

* * * * *